(12) United States Patent
Ionascu et al.

(10) Patent No.: US 8,539,948 B2
(45) Date of Patent: Sep. 24, 2013

(54) HYPERTHERMIA ASSISTED RADIATION THERAPY

(75) Inventors: Dan Ionascu, West Bloomfield, MI (US); Brian Marples, Farmington Hills, MI (US); Di Yan, Auburn Hills, MI (US); Alvaro Martinez, Bloomfield Hills, MI (US)

(73) Assignee: William Beaumont Hospital, Royal Oak, MI (US)

( * ) Notice: Subject to any disclaimer, the term of this patent is extended or adjusted under 35 U.S.C. 154(b) by 326 days.

(21) Appl. No.: 12/782,323

(22) Filed: May 18, 2010

(65) Prior Publication Data

US 2010/0294279 A1    Nov. 25, 2010

Related U.S. Application Data

(60) Provisional application No. 61/216,587, filed on May 19, 2009.

(51) Int. Cl.

| A61M 16/00 | (2006.01) |
|---|---|
| A62B 7/00 | (2006.01) |
| A62B 18/08 | (2006.01) |
| F24J 3/00 | (2006.01) |
| A61B 19/00 | (2006.01) |
| A61F 7/00 | (2006.01) |

(52) U.S. Cl.
USPC .............. 128/204.17; 128/201.13; 128/898; 607/104

(58) Field of Classification Search
USPC .......... 128/203.12, 203.13, 203.26, 203.27, 128/204.15–204.18, 204.21, 204.22, 205.12, 128/205.27, 898, 201.13; 607/96, 104, 105, 607/107, 113
See application file for complete search history.

(56) References Cited

U.S. PATENT DOCUMENTS

| 6,131,571 | A | 10/2000 | Lampotang et al. |
|---|---|---|---|
| 6,523,538 | B1 | 2/2003 | Wikefeldt |
| 7,525,663 | B2 * | 4/2009 | Kwok et al. .................. 356/436 |
| 2006/0037613 | A1 | 2/2006 | Kwok et al. |
| 2007/0157929 | A1 | 7/2007 | Radomski et al. |
| 2008/0142010 | A1 * | 6/2008 | Weaver et al. ........... 128/203.26 |
| 2008/0216835 | A1 | 9/2008 | McGinnis et al. |
| 2009/0000620 | A1 | 1/2009 | Virr |
| 2009/0038615 | A1 | 2/2009 | Bradley |

FOREIGN PATENT DOCUMENTS

| EP | 1138341 A2 | 10/2001 |
|---|---|---|
| WO | 97/31670 A1 | 9/1997 |
| WO | WO03/018096 A1 | 3/2003 |
| WO | 2004020031 A1 | 3/2004 |
| WO | WO2008/076230 A2 | 6/2008 |

OTHER PUBLICATIONS

Norman M. Bleehen, Role of Hyperthermia in Treatment of Lung Cancer, Cancer Treatment Symposia 2: 75-9 (1985).*

(Continued)

*Primary Examiner* — Melanie Hand
*Assistant Examiner* — Mark K Han
(74) *Attorney, Agent, or Firm* — Honigman Miller Schwartz and Cohn LLP; Douglas H. Siegel; Jonathan P. O'Brien

(57) ABSTRACT

A breathing system for hyperthermic assisted radiation therapy includes at least one heating element that modulates the temperature of air inhaled by a patient, at least one cooling element that modulates the humidity of the air inhaled by a patient, and a controller that maintains the desired humidity and temperature.

8 Claims, 6 Drawing Sheets

(56) References Cited

OTHER PUBLICATIONS

Westermann,A.M. et al. First results of triple-modality treatment combining radiotherapy, chemotherapy, and hyperthermia for the treatment of patients with stage IIB, III, and IVA cervical carcinoma. *Cancer* 104, 763-770 (2005).
Hehr,T., Wust,R., Bamberg,M. & Budach,W. Current and potential role of thermoradiotherapy for solid tumours. *Onkologie* 26, 295-302 (2003).
Dewhirst,M.W., Vujaskovic,Z., Jones,E. & Thrall,D. Re-setting the biologic rationale for thermal therapy. *International Journal of Hyperthermia* 21, 779-790 (2005).
van der Zee,J. Heating the patient: a promising approach? *Annals of Oncology* 13, 1173-1184 (2002).
Jones,E.L. et al. Randomized trial of hyperthermia and radiation for superficial tumors. *Journal of Clinical Oncology* 23, 3079-3085 (2005).
Wust,P. et al. Hyperthermia in combined treatment of cancer. *Lancet Oncology* 3, 487-497 (2002).
Menoret,A. & Chandawarkar,R. Heat-shock protein-based anticancer immunotherapy: An idea whose time has come. *Seminars in Oncology* 25, 654-660 (1998).
Tamura,Y., Peng,P., Liu,K., Daou,M. & Srivastava,P.K. Immunotherapy of tumors with autologous tumor-derived heat shock protein preparations. *Science* 278, 117-120 (1997).
Suto,R. & Srivastava,P.K. A Mechanism for the Specific Immunogenicity of Heat-Shock Protein-Chaperoned Peptides. *Science* 269, 1585-1588 (1995).
DahmDaphi,J., Brammer,I. & Dikomey,E. Heat effects on the repair of DNA double-strand breaks in CHO cells. *International Journal of Radiation Biology* 72, 171-179 (1997).
Dikomey,E. & Jung,H. Correlation Between Thermal Radiosensitization and Slowly Rejoined DNA Strand Breaks in Cho Cells. *International Journal of Radiation Biology* 68, 227-233 (1995).
Dikomey,E. & Franzke,J. Effect of Heat on Induction and Repair of DNA Strand Breaks in X-Irradiated Cho Cells. *International Journal of Radiation Biology* 61, 221-233 (1992).
Spiro,I.J., Denman,D.L. & Dewey,W.C. Effect of Hyperthermia on Cho DNA-Polymerases Alpha and Beta. *Radiation Research* 89, 134-149 (1982).
Livingstone,S.D., Nolan,R.W., Cain,J.B. & Keefe,A.A. Effect of Working in Hot Environments on Respiratory Air Temperatures. *European Journal of Applied Physiology and Occupational Physiology* 69, 98-101 (1994).
Atkins,K.J., Thompson,M.W., Ward,J.J. & Kelly,P.T. Expired air temperature during prolonged exercise in cool- and hot-humid environments. *European Journal of Applied Physiology and Occupational Physiology* 76, 352-355 (1997).
Aoyagi,Y., McLellan,T.M. & Shephard,R.J. Interactions of physical training and heat acclimation—The thermophysiology of exercising in a hot climate. *Sports Medicine* 23, 173-210 (1997).
de Senneville,B.D., Quesson,B. & Moonen,C.T.W. Magnetic resonance temperature imaging. *International Journal of Hyperthermia* 21, 515-531 (2005).
Gellermann,J. et al. Methods and potentials of magnetic resonance imaging for monitoring radiofrequency hyperthermia in a hybrid system. *International Journal of Hyperthermia* 21, 497-513 (2005).
Ishihara,Y. et al. Precise and Fast Temperature Mapping Using Water Proton Chemical-Shift. *Magnetic Resonance in Medicine* 34, 814-823 (1995).
Galiana,G., Branca,R.T., Jenista,E.R. & Warren,W.S. Accurate temperature imaging based on intermolecular coherences in magnetic resonance. *Science* 322, 421-424 (2008).
Mclemore,T.L. et al. Comparison of Intrapulmonary, Percutaneous Intrathoracic, and Subcutaneous Models for the Propagation of Human Pulmonary and Nonpulmonary Cancer Cell-Lines in Athymic Nude-Mice. *Cancer Research* 48, 2880-2886 (1988).
Mclemore,T.L. et al. Novel Intrapulmonary Model for Orthotopic Propagation of Human-Lung Cancers in Athymic Nude-Mice. *Cancer Research* 47, 5132-5140 (1987).
Hildebrandt B, Wust P. Interactions between hyperthermia and cytotoxic drugs. *Cancer Treat.Res.*2007;134:185-93. PMID: 17633054.
Karino T, Koga S, Maeta M. Experimental studies of the effects of local hyperthermia on blood flow, oxygen pressure and pH in tumors. *Jpn.J.Surg.* 1988;18:276-83. PMID: 3404776.
Maeta M, Karino T, Inoue Y, Hamazoe R, Shimizu N, Koga S. The effect of angiotensin II on blood flow in tumours during localized hyperthermia. *Int.J.Hyperthermia* 1989;5:191-7. PMID: 2926185.
Horsman MR, Overgaard J. Can mild hyperthermia improve tumour oxygenation? *Int.J.Hyperthermia* 1997;13:141-7. PMID: 9147141.
Sorensen BS, Horsman MR, Vorum H, Honore B, Overgaard J, Alsner J. Proteins upregulated by mild and severe hypoxia in squamous cell carcinomas in vitro identified by proteomics. *Radiother.Oncol.*2009;92:443-9. PMID: 19541378.
Hiraoka M, Masunaga S, Nishimura Y, Nagata Y, Jo S, Akuta K et al. Regional Hyperthermia Combined with Radiotherapy in the Treatment of Lung Cancers. *International Journal of Radiation Oncology Biology Physics* 1992;22:1009-14. PMID: 1313403.
Ohguri T, Imada H, Yahara K, Morioka T, Nakano K, Terashima H et al. Radiotherapy with 8-Mhz Radiofrequency-Capacitive Regional Hyperthermia for Stage Iii Non-Small-Cell Lung Cancer: the Radiofrequency-Output Power Correlates with the Intraesophageal Temperature and Clinical Outcomes. *International Journal of Radiation Oncology Biology Physics* 2009;73:128-35. PMID: 18513887.
Corry PM, Armour EP. The heat shock response: role in radiation biology and cancer therapy. *Int.J.Hyperthermia* 2005;21:769-78. PMID: 16338860.
Sekins KM, Leeper DB, Hoffman JK, Wolfson MR, Shaffer TH. Feasibility of lung cancer hyperthermia using breathable perfluorochemical (PFC) liquids. Part I: Convective hyperthermia. *Int.J.Hyperthermia* 2004;20:252-77. PMID: 15204525.
Sekins KM, Leeper DB, Hoffman JK, Keilman GW, Ziskin MC, Wolfson MR et al. Feasibility of lung cancer hyperthermia using breathable perfluorochemical (PFC) liquids. Part II: Ultrasound hyperthermia. *Int.J.Hyperthermia* 2004;20:278-99. PMID: 15204526.
Corry PM, Jabboury K, Kong JS, Armour EP, McCraw FJ, Leduc T. Evaluation of equipment for hyperthermic treatment of cancer. *Int.J.Hyperthermia* 1988;4:53-74. PMID: 3346584.
Travis EL. The Sequence of Histological-Changes in Mouse Lungs After Single Doses of X-Rays. *International Journal of Radiation Oncology Biology Physics* 1980;6:345-7. PMID: 7390907.
Johnston CJ, Williams JP, Elder A, Hernady E, Finkelstein JN. Inflammatory cell recruitment following thoracic irradiation. *Experimental Lung Research* 2004;30:369-82. PMID: 15204829.
Rubin P, Finkelstein J, Shapiro D. Molecular-Biology Mechanisms in the Radiation Induction of Pulmonary Injury Syndromes—Interrelationship Between the Alveolar Macrophage and the Septal Fibroblast. *International Journal of Radiation Oncology Biology Physics* 1992;24:93-101. PMID: 1512168.
Hong JH, Chiang CS, Tsao CY, Lin PY, McBride WH, Wu CJ. Rapid induction of cytokine gene expression in the lung after single and fractionated doses of radiation. *International Journal of Radiation Biology* 1999;75:1421-7. PMID: 10597915.
Rubin P, Johnston CJ, Williams JP, Mcdonald S, Finkelstein JN. A Perpetual Cascade of Cytokines Postirradiation Leads to Pulmonary Fibrosis. *International Journal of Radiation Oncology Biology Physics* 1995;33:99-109. PMID: 7642437.
Mcdonald S, Rubin P, Phillips TL, Marks LB. Injury to the Lung from Cancer-Therapy—Clinical Syndromes, Measurable End-Points, and Potential Scoring Systems. *International Journal of Radiation Oncology Biology Physics* 1995;31:1187-203. PMID: 7713782.
Ashcroft T, Simpson JM, Timbrell V. Simple Method of Estimating Severity of Pulmonary Fibrosis on a Numerical Scale. *Journal of Clinical Pathology* 1988;41:467-70. PMID: 3366935.

Kasper M, Haroske G. Alterations in the alveolar epithelium after injury leading to pulmonary fibrosis. Histology and Histopathology 1996;11:463-83. PMID: 8861769.

Craciunescu OI, Stauffer PR, Soher BJ, Wyatt CR, Arabe O, Maccarini P et al. Accuracy of real time noninvasive temperature measurements using magnetic resonance thermal imaging in patients treated for high grade extremity soft tissue sarcomas. Med.Phys. 2009;36:4848-58. PMID: 19994492.

* cited by examiner

HYPERTHERMIA ASSISTED RADIATION THERAPY

RELATED APPLICATION

This application claims the benefit of U.S. Provisional Application No. 61/216,587, filed May 19, 2009, the entire contents of which are incorporated herein by reference.

BACKGROUND

The present invention relates generally to radiation therapy. More particularly, the present invention relates to hyperthermia assisted radiation therapy.

Lung cancer is the most common fatal cancer in the United States for men aged 40 years and older and women aged 60 years and older. Inoperable lung tumors are primarily treated using radiation therapy. Recent studies in radiation therapy of lung tumors have shown that higher radiation dose delivered to the target has been associated with improved tumor control. However, a major therapeutic concern is represented by tumor hypoxia where hypoxic cells require three times more dose than a well oxygenated cell to achieve the same level of cell deaths. When cells gradually become hypoxic they adapt by up-regulating the production of numerous proteins that promote their self-survival. These proteins slow the rate of growth, stimulate growth of new vasculature, inhibit apoptosis, and promote metastatic spread. The direct consequence of these changes is that patients with hypoxic tumors invariably experience poor outcome to treatment, hypoxia also being the primary inhibitor of chemotherapy effectiveness.

BRIEF SUMMARY

In view of the drawbacks and limitations of the known technologies, a breathing system for hyperthermic assisted radiation therapy (HART) includes at least one heating element that modulates the temperature of air inhaled by a patient, at least one cooling element that modulates the humidity of the air inhaled by a patient, and a controller that maintains the desired humidity and temperature in accordance with the invention.

Some embodiments may include one or more of the following advantages:

The HART technique generates a better local tumor control with significant, synergistic enhancement of clinical outcome. The method can reduce the number of treatment fractions due to the enhanced local tumor control. The breathing system can be integrated with a linear accelerator. As such, along with image guidance, the online data provided by the system allows the medical personnel to explore several gating strategies based on the separate or combinations of breathing parameters. This in turn can add to the synergistic effect of HART. The HART technique can improve patient well being during the treatment. The system and method will not interrupt the current treatment flow, requires no additional dose to the patient and presents only minimal risk. Modern breathing systems precisely synchronize ventilation to the patient's breathing requirements, helping to minimize the work of breathing and therefore assisting the patients in achieving a calm, regular breathing state.

The system can be a portable, robust technology to safely induce hyperthermia at the lungs tissue level as an adjuvant treatment to be delivered simultaneously with radiotherapy. The developed technology can be the basis for enhancing the clinical outcome by combining HART with adjuvant therapies relying on compatible radiosensitizers for lung tumors.

The foregoing discussion has been provided only by way of introduction. Additional features, benefits and advantages of the present invention will become apparent from the subsequent description and the appended claims, taken in conjunction with the accompanying drawings.

BRIEF DESCRIPTION OF THE DRAWINGS

The accompanying drawings, incorporated in and forming a part of the specification, illustrate several aspects of the present invention and, together with the description, serve to explain the principles of the invention. The components in the figures are not necessarily to scale. Moreover, in the figures, like reference numerals designate corresponding parts throughout the views. In the drawings.

DETAILED DESCRIPTION

Major benefits may be achieved by the addition of heat to radiation therapy and chemotherapy. Heat-induced biological effects act as strong adjuvant for the radiation therapy and are effectively used in cancer treatment to kill cancer cells at different stages of growth. Heat-mediated tumor reoxygenation is attributed to increased vascularization and increase in oxygen local pressure ($pO_2$). Also, the damage repair mechanisms are inhibited where induction of chromosomal aberrations increased with heat-induced radiosensitization. Hyperthermia may be able to modulate the immune system by inducing the expression of heat-shock proteins (HSP). HSP isolated from cancer cells are able to induce a cytotoxic T-cell-activation against the tumor. Moreover, there is a temperature-dependant inhibition of DNA-repair enzymes, DNA-polymerases-$\alpha$ and -$\beta$. Accordingly, because of the anatomy and physical properties of the lung, there is a need to elevate and control the lung tissue temperature at levels needed to induce the radiosensitizing response.

Figure 1:
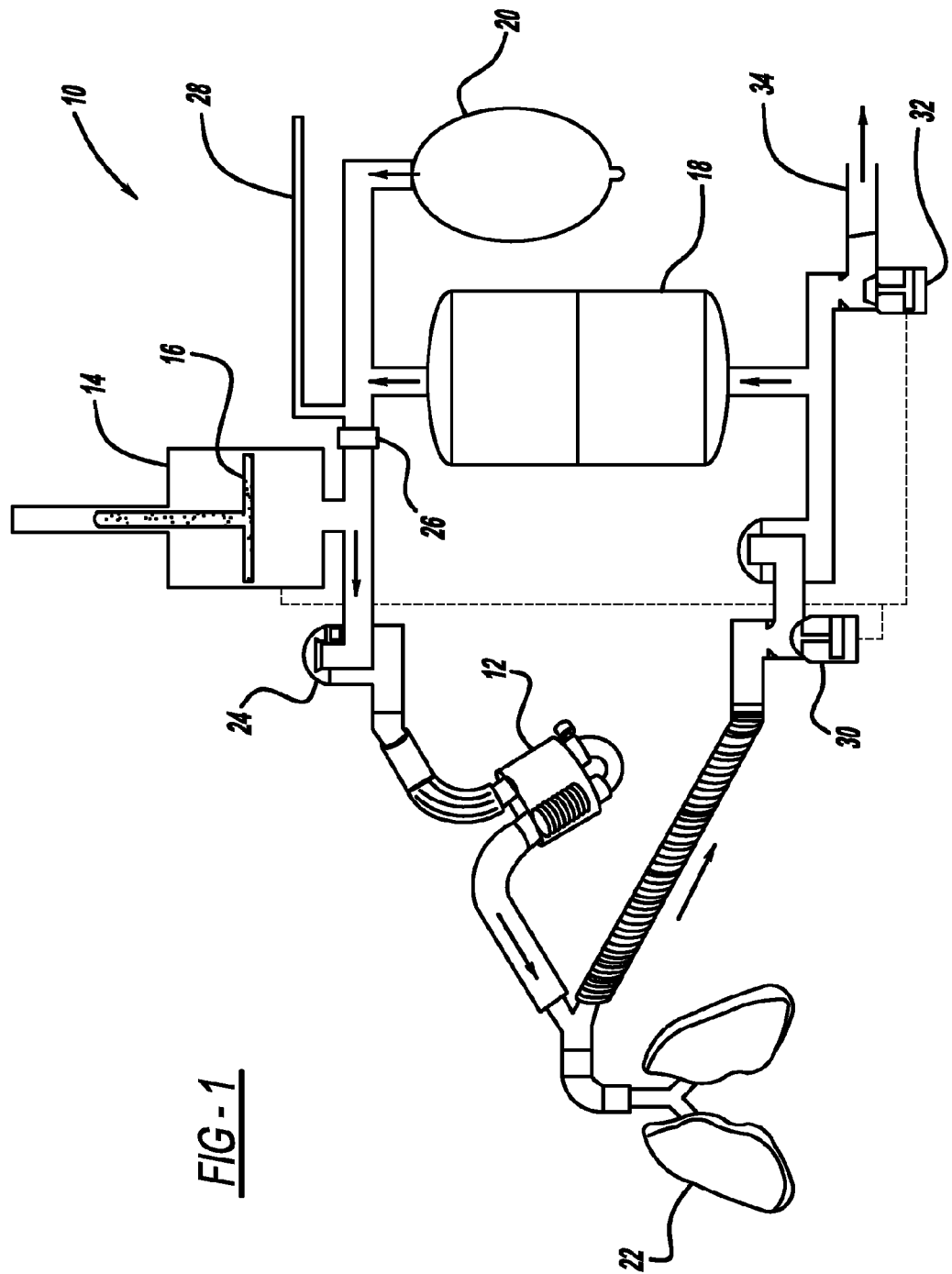
FIG. 1 shows a breathing system design including a temperature and humidity controller in accordance with the invention.
Figure 2:
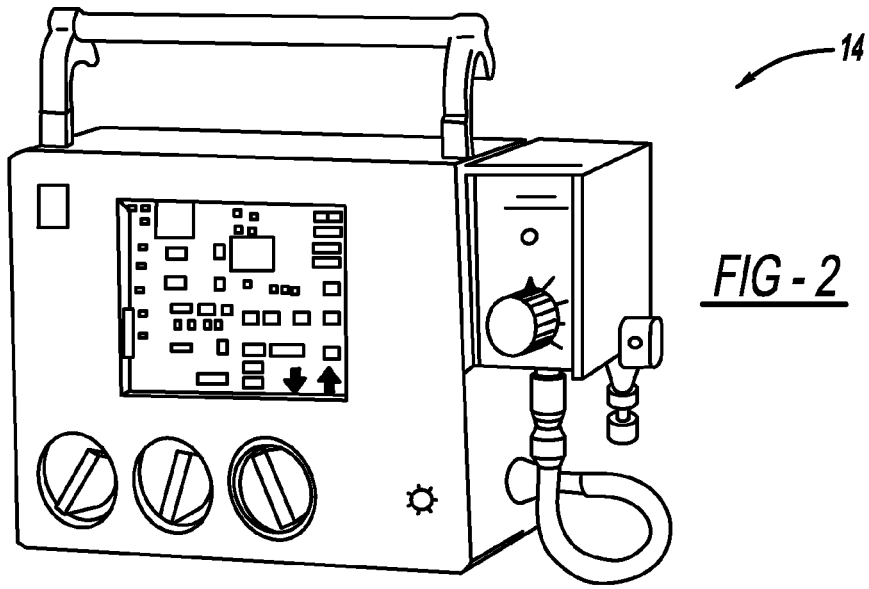
FIG. 2 shows a portable continuous positive airway pressure (CPAP) ventilator with $O_2$ mixers.
Figure 4:
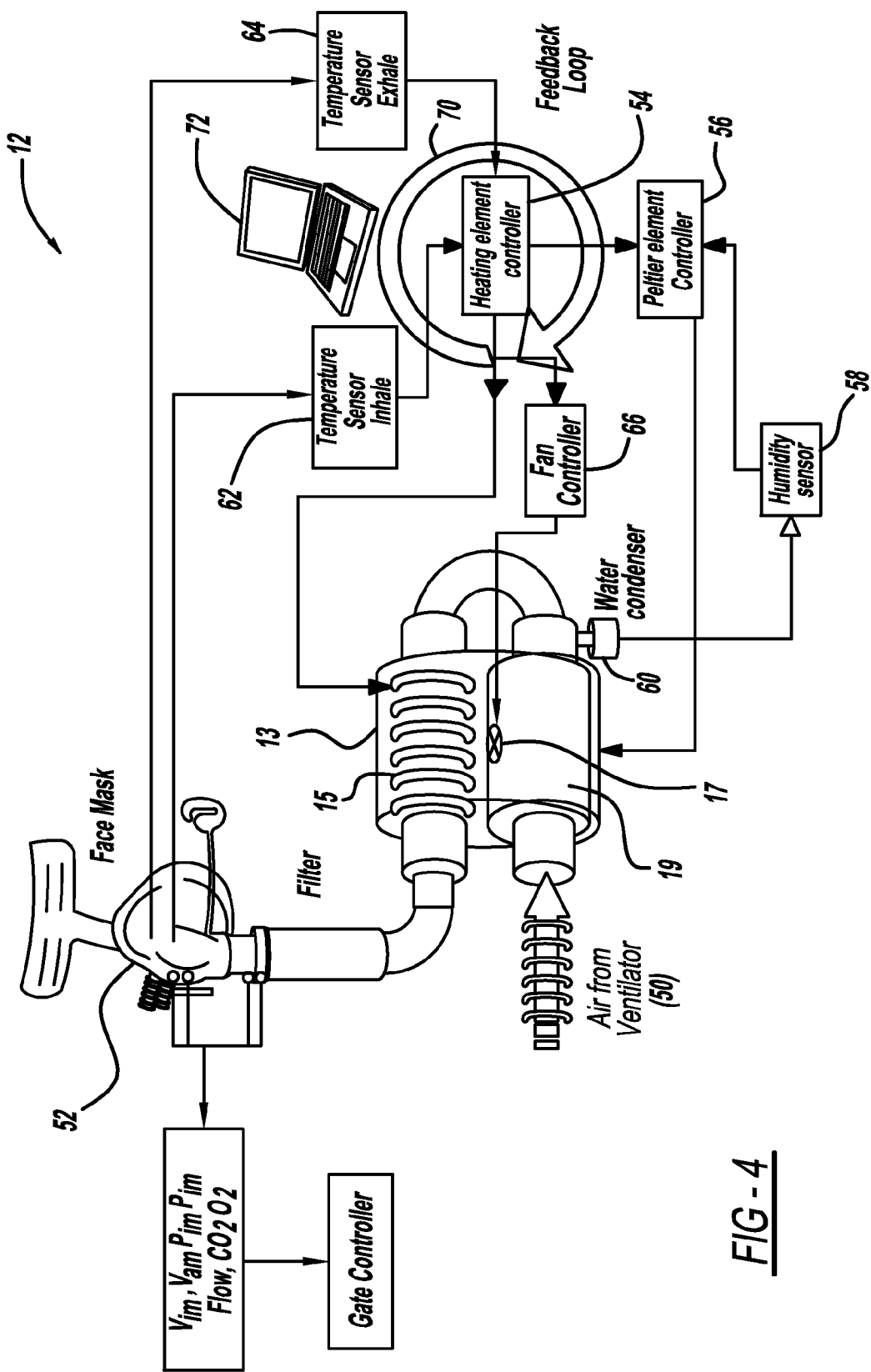
FIG. 4 is a detail view of the temperature and humidity controller of FIG. 1 used to control temperature and humidity of the inhale air in accordance with an embodiment of the present invention.

Referring now to FIG. 1, a breathing system embodying the principles of the present invention is illustrated therein and designated at 10. As its primary components, the system 10 includes a temperature and humidity controller 12, a ventilator 14 with a ventilator piston 16, an absorbent canister 18, and a reservoir 20. An intake valve 24 and a decoupling valve 26 control the flow of air through the temperature and humidity controller 12 to the patient's lungs 22, typically through a mask 52 (FIG. 4), while a pair of exhaust or exhalation valves 30, 32 in coordination with the ventilator 14, control the exhaust exhaled from the patient's lungs 22.

Fresh air is supplied through an inflow line 28 and flows directly to the lungs 22 and also fills the reservoir 20 which supplies further fresh air when needed. The exhaust from the lungs 22 are expelled from the system 10 through an exhaust line 34 when the exhaust valves 30 and 32 are open. The exhaled air may also be directed to the absorbent canister 18 when the valve 32 is closed.

To further improve the clinical outcome in the case of lung tumors, the air the patient breathes is a thermal delivery vector to induce hyperthermia at the lung tissue level. Moreover, the vector can be used to efficiently deliver specific radiosensitizers mixed in the breathing air. Therefore a robust breathing system controls the temperature of the lung tissue within the hyperthermic regime (about 41-43° C.) in accordance with the invention.

Local tumor control is accomplished by exposing the lung tumors to a synergetic cancer treatment system that encompasses the use of hyperthermia and specific radiosensitizing factors in addition to the conventional dosimetric escalation and cytotoxic drugs. Hyperthermia assisted radiation therapy (HART) provides enhanced local tumor control for lung cancer disease.

Because of the heat-mediated tumor reoxygenation, radiosensitizers are gas mixtures that contain elevated concentrations of oxygen (hyperoxic gas). Damage to DNA is primarily induced by interaction with oxygen radicals (for example, hydroxyl radical, superoxide anion) formed by the ionization of water surrounding the DNA. The damaged ends of DNA can react with the nearby oxygen to form stable, organic peroxides that are difficult repair, increasing the mitotic death propensity. A higher oxygen concentration in the inhaled air results in increased blood oxygen concentration. Alternatively, a combination of hyperoxic gases and vasodilating drugs can be also used. Reversely, in the case of radiotherapy treatments for tumors located in the upper abdomen (liver, pancreas), where the lungs are organs at risk for radio-contamination, the breathing device (in the no-heat regime) can be used to deliver lung-specific radioprotectants.

The breathing system 10 is capable of safely raising and controlling the temperature of the lung tissue with minimal disruption of the present treatment flow. The temperature of the lung tissue is measured and calibrated non-invasively using magnetic resonance temperature imaging (MRI thermometry). The system 10 provides targeted radiosensitizers for lung tumors that can be safely aerosolized and mixed in the breathing air.

The ventilator 14 has continuous positive airway pressure (CPAP) control which is regulated by a restriction of flow to the exhalation valve 30. CPAP provides continuous positive airway pressure in the breathing circuit as the patient breathes spontaneously. This keeps the alveoli and airways inflated by preventing proximal airway pressure from returning to zero at the end of exhalation. CPAP is applied to patients who can breathe spontaneously and do not require full ventilatory support. It can improve lung volume and, consequently, oxygenation and lung function by increasing alveolar volumes, recruitment, and stability. By helping to redistribute interstitial water, CPAP also improves $O_2$ diffusion across the alveolar capillary membrane.

Referring to FIG. 2, there is shown a CRAP ventilator 14 that provides a computer interface for data acquisition. Such systems can provide the general thermodynamic breathing parameters (exhale/inhale volume, pressure, $O_2$ concentration) during the radiotherapy treatment. They also deliver gas mixtures at controllable concentrations. An infrared transducer and a visible spectrum transducer can be integrated in the breathing mask to measure the $CO_2$ and $O_2$ concentrations. The parameters are recorded by a central acquisition system, such as, for example, the NI (National Instruments Corporation, Austin, Tex.) platform that includes the data acquisition hardware (DAQ) and the controlling software, which provides a user interface to monitor and record the respiratory parameters as shown, for example, in FIG. 3.

Referring FIG. 4, further details of the temperature and humidity controller 12 are illustrated. The temperature and humidity controller 12 receives air from the ventilator as indicated by the arrow 50 and supplies air at the desired temperature and humidity to a mask 52 worn by the patient who inhales the treated air. The temperature and humidity controller 12 further includes a heating element controller 54 and a Peltier element controller 56 to adjust or modulate the temperature and humidity, respectively, of the inflowing air. The humidity of the air is monitored by a humidity sensor 58 which receives signals from a water condenser 60. The signal from water condenser 60 indicates the amount of water in the fresh air flowing from the ventilator. The temperature and humidity controller 12 also includes an inhalation temperature sensor 62 and an exhalation temperature sensor 64 that monitors the inlet and exhaust temperature to and from the patient, respectively. The information from the sensors 62 and 64 are fed to the heating element controller 54 which in conjunction with a fan controller adjusts the fresh air to the desired temperature. The temperature sensors 62, 64, the humidity sensor 58, the Peltier element controller 56, the heating element controller 54, and the fan controller 66 provide information to a feedback system or loop 70 under the direction of a CPU such as, for example, a computer 72. The sensors 62 and 64 may be located in the mask 52. The humidity sensor 58, the Peltier element controller 56, the heating element controller 54, and the fan controller 66 may be contained in a housing 13 which also contains the heating elements 15, a fan 17, and Peltier cooling elements 19.

The temperature and humidity control system 12 allows the patient to freely breathe air at temperatures between about 45° C. to 55° C. (with minimal effort). This will induce a thermal steady state (TSS) in the lung tissue with temperatures in the range of about 41° C. to 43° C. The feedback loop 70 modulates the relationship between the inhaled air temperature and the exhaled air temperature to achieve a thermal steady state inside the lungs. The lung thermal steady state is defined as the state where the exhale air temperature is within the range of about 41° C. to 43° C. hyperthermic regime. Once a relative steady state is attained, the radiotherapy treatment is ready to be initiated.

The lung tissue temperature varies as a function of the respiratory inhalation or exhalation phase. Because of the lung physiology, the range of temperature fluctuations can also be influenced by controlling the relative humidity (RH) inhaled air. The higher the humidity the smaller is the difference between inhaled and exhaled air temperatures as indicated in FIG. 5. In particular, FIG. 5 shows the relative humidity effect on temperature of the exhaled air. It is desirable to achieve a relative steady state with temperature variations confined within the hyperthermic regime (of about 41° C. to 43° C.). However, the relative humidity effect is analyzed and controlled since humid air (RH>70%) is more difficult to breathe and lung cancer patients often have reduced respiratory function. Accordingly, an optimal combination between air temperature and relative humidity is desired to comfort patients' needs. Nevertheless, RH typically does not exceed about 65%. Preferably, the RH is about 60%.

Humidity control with the Peltier element controller 56 is achieved with the series of cascaded Peltier cooling elements 19 (thermoelectric effect), which cool down the incoming gas to facilitate water condensation that collects in the water condenser 60. The air humidity is measured by the humidity sensor 58 and constantly read by the feedback system or loop 70. In turn, the feedback loop 70 controls the current that feeds the cooling system to achieve the appropriate humidity level. For the cooling system to work efficiently, the 'hot' side is appropriately vented. This is accomplished by using the cooling fan 17, under the direction of the fan controller 66, which directs the heat generated by the Peltier elements 19 towards the air heating region of the system. Since air cooling efficiency depends on how fast heat is transported away, the fan speed is also controlled by the feedback loop 70. Based on the temperature of the exhaled air, as detected by the exhalation temperature sensor 64, the feedback loop 70 controls the air heating elements 15. The feedback controller within, for example, the computer 72, features proportional, integral, and derivative (PID) control that provides exceptionally tight control of air temperature and humidity. The feedback algorithm contains an auto-tuning feature that helps to ensure maximum performance over a broad spectrum of operating conditions (for example, fast/slow rate breathing and shallow/deep breathing). Auto-tuning sets the critical PID terms to match the conditions of the application and provides fast response while minimizing overshoot and undershoot. A couple of sensor alarms that monitor the upper temperature and humidity limits are located at the inhalation terminal and at the air heating controller. Their roles are redundant with the feedback loop sensors and provide an emergency switch-off function if temperature and/or humidity exceed the preset upper limit.

In another arrangement, the humidity sensor is located in the mask 52. Signals are sent from the humidity sensor in the mask directly to the heating element controller 54. In turn, information from the heating element controller 54 is sent to the Peltier element controller 56 which adjusts the amount of vaporization occurring in the housing 13, where the water condenser 60 may act as a reservoir for humidification of the air.

Figure 5:
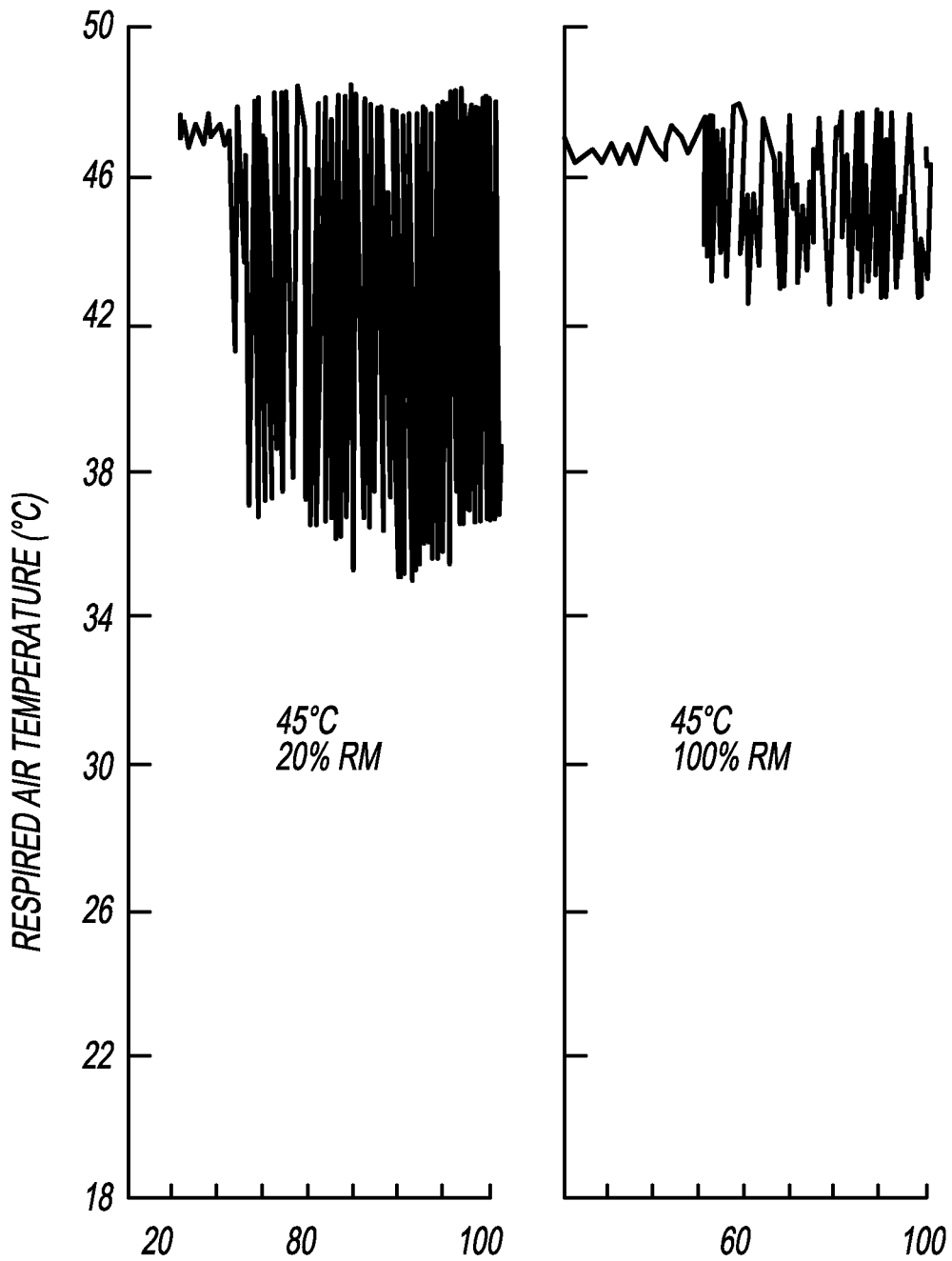
FIG. 5 shows the effect of relative humidity on the temperature of the exhaled air.

As shown in FIG. 5, the exhaled air temperature, can easily reach temperatures needed to induce a hyperthermic regime at the lung tissue level. However, the temperature of the lung tissue may depend on how deep the patient breathes. To address this, a series of non-invasive, MRI thermometry analyses under different respiratory conditions (temperature, humidity, oxygen concentration and breathing depth) is performed. The approach to clinical MR thermometry uses the change in resonance frequency of water protons with temperature or selective detection of intermolecular multiple quantum coherences. The data obtained is employed to calibrate the temperature control feedback loop 70 in order to obtain the optimal set of parameters necessary to induce the hyperthermic response.

The following examples illustrated features and principles of the present invention but are not meant to limit the scope of the present invention.

EXAMPLE 1

In Vitro Investigation of HART Applied to Lung Adenocarcinoma Cells

Figure 6:
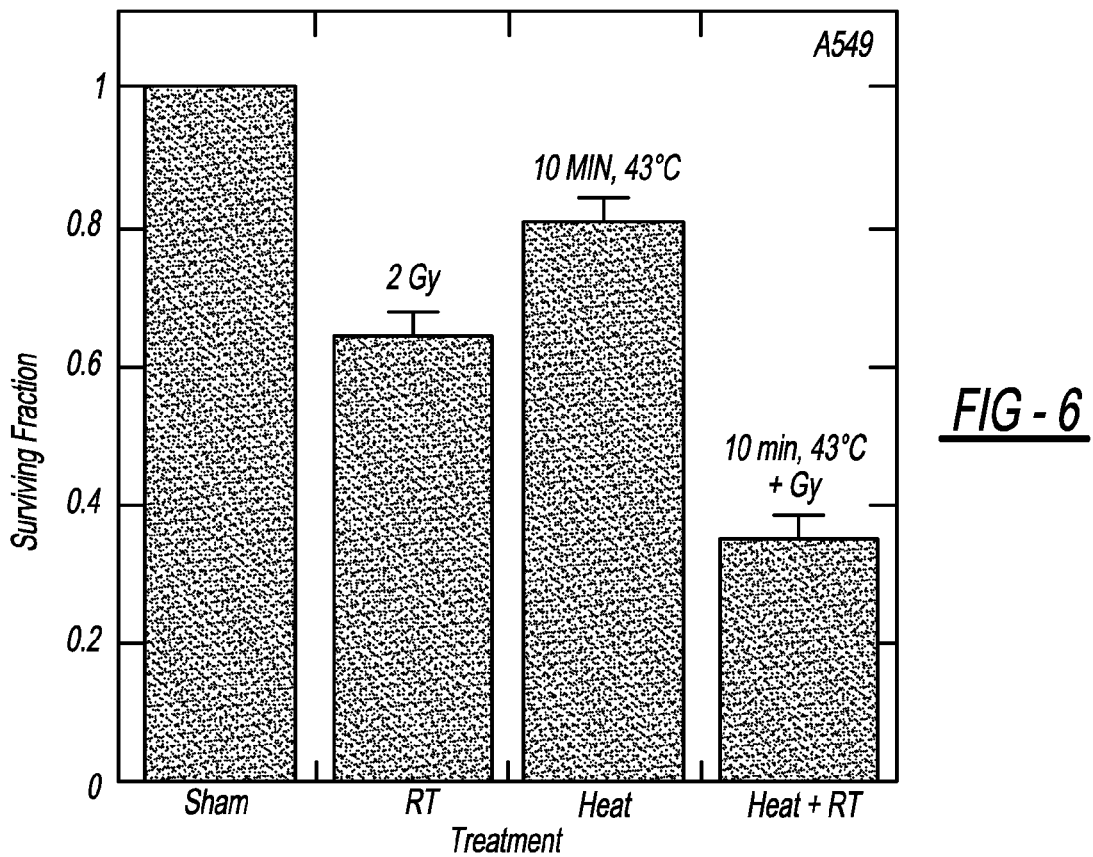
FIG. 6 shows radiosensitization after simultaneous 2 Gy X-irradiation and 10 minute heat treatment.

Modest sensitization of A549 lung adenocarcinoma cells was evident after a 10 min treatment of 45° C. (surviving fraction (SF)=0.81±0.03). This was markedly increased by 30 minute (SF=0.12±0.01) and 60 minute treatments (SF=0.002±0.0001). Radiosensitization was demonstrated after 2 Gy X-irradiation with simultaneous heat exposures. Survival was reduced from 0.81±0.03 (heat only) to 0.34±0.03 (heat+radiation) for a 10 minute thermal treatment (FIG. 6) and from 0.12±0.01 (heat only) to 0.01±0.002 (heat+radiation) for 30 minute thermal treatment. By comparison, a single x-ray dose reduced survival to 0.64±0.03.

These thermal-radiosensitizing effects may translate into a complex 3D tissue model to establish and define the role of blood flow in regulating temperature in solid pulmonary tumors and surrounding normal lung tissue. A murine model was used for pragmatic reasons of cost and to utilize the small animal imaging device (described below). Simultaneous radiation and heat is given to ensure thermal radiosensitization, rather than additional thermal cytotoxicity that is obtained when hyperthermia is given pre or post irradiation.

EXAMPLE 2

In Vivo Investigation of HART Applied to Small Animals

Figure 7:
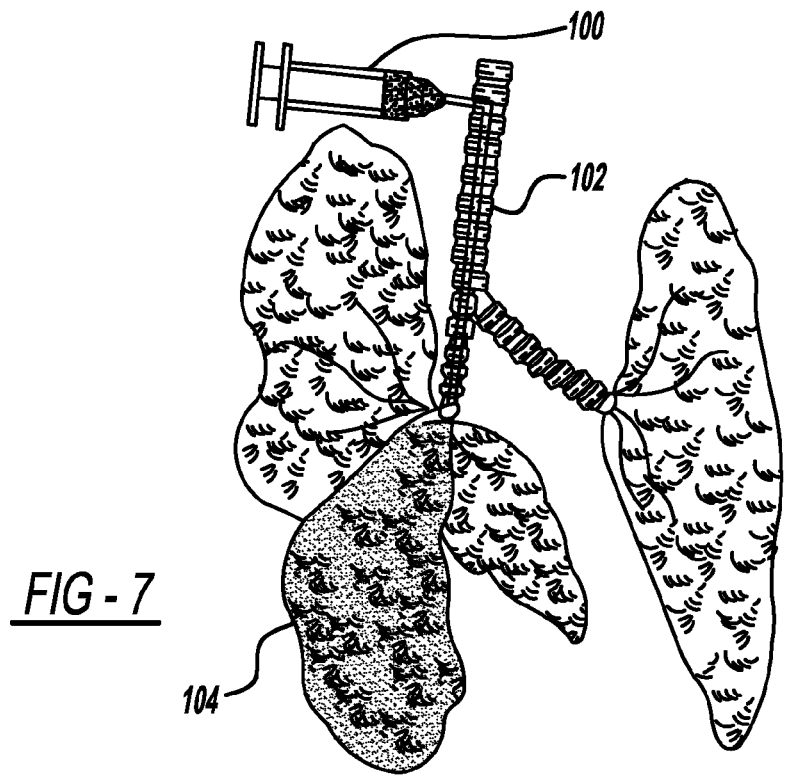
FIG. 7 shows an intrabronchial (i.b.) implantation technique.

A model using orthotopic implanted human pulmonary tumors can be employed. The A549 adenocarcinoma cells were chosen for a previous in vivo tumor growth delay studies because these tumors are relatively resistant to many cancer therapies and are highly metastatic to the lungs from subcutaneous implants. However, tumors can be established directly in the lungs of female nude mice. As shown in FIG. 7, an implantation technique for the growth of human lung cancer cell lines in the bronchioloalveolar region of the right lung via intrabronchial (i.b.) injection with a syringe 100 into the bronchial tubes 102 is employed. The shaded area 104 in FIG. 7 represents the caudal lobe of the right lung, the area where the majority of tumor cells are localized following i.b. implantation. Tumor-bearing animals implanted with this technique become progressively cachexie and dyspneic following implantation. Tumors grow predominately in the pleural space and subsequently invaded the lung parenchymal and/or chest wall structures. An overall tumor-related mortality of 92% is observed within 50 days after a $1\times10^6$ A549 tumor cell inoculum. Local mediastinal invasion is observed. Animals bearing the lung carcinomas can be treated with localized pulmonary X-irradiation targeted to the tumor site using a 160 KVp Faxitron X-ray cabinet (model 43855F, Wheeling, Ill.). Three fractions of 5 Gy is given over five days to mimic clinical hypofractionation schedules. Radiation treatment occurs on days 7-11 post-tumor cell implantation when the tumors are about 100 $mm^3$ in volume. Tumor volume will be determined by SPECT/CT imaging using a GammaMedica FLEX Triumph™ system small animal imager. Blood flow is considered with respect to the extent of tumor hypoxia as determined by PET scans using $^{F18}FDG$. Throughput for PET/CT is 5-15 animals depending on the protocol, and SPECT/CT is 2-20 animals depending on the protocol. Imaging is used to target the pulmonary irradiations. The primary endpoint is tumor volume. Treatment efficacy for RT alone, 10 minutes air-breathing at 45° C. alone and simultaneous RT combined with 10 minutes air-breathing at 45° C. is statistically compared. A final group of animals is sham treated for determine untreated tumor growth rate. RT only animals is exposed to the same breathing regimen and the hyperthermia animals excluding the heating, while heat only animals is sham-irradiated. To allow for variation in tumor growth rates and tumor take rates between animals 20 animals per treatment group are employed.

Figure 8:
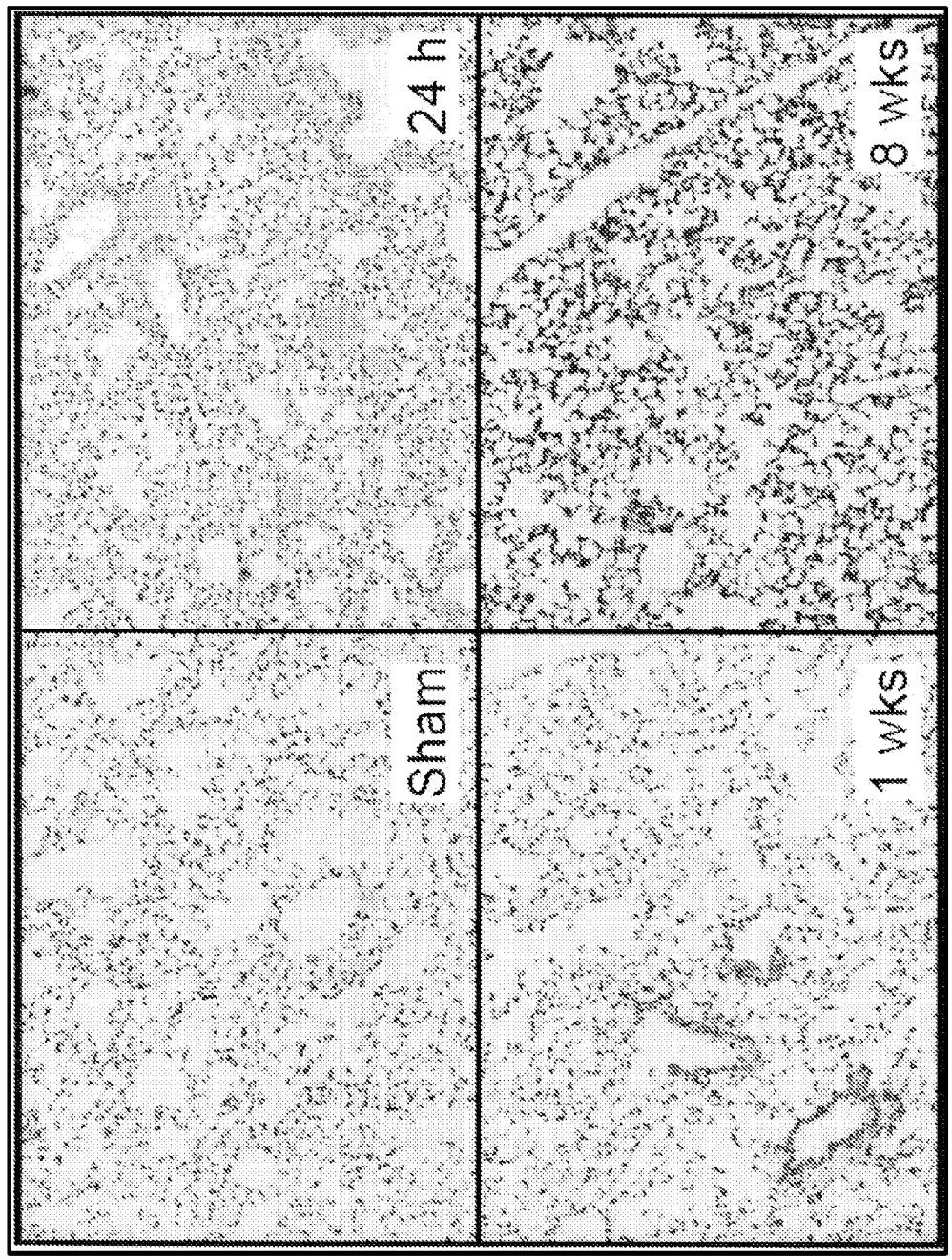
FIG. 8 shows haematoxylin and eosin stained lung sections showing representative changes in alveolar structure with time after irradiation.

The lungs are isolated from all treated animals and examined for therapy-related changes to histology compared with sham-treated controls. FIG. 8 illustrates the change in lung architecture for haematoxylin and eosin stained lung sections that is seen 48 hours and 4 weeks post irradiation with a single dose of 2 Gy X-rays in the absence of heat. The lung sections show representative changes in alveolor structure with time after irradiation. The largest increases in alveolar septa can be seen at the early times after radiation exposure. These include thickening of the alveolar septa and invasion of inflammatory cells.

An automated mathematical scoring algorithm was developed based on segmentation analysis to determine the extent of pulmonary injury that is used to classify injury in this study. This is employed in combination with physical measurements of alveolar septal thickness obtained from H&E high magnification microscopy (40× objective) and a manual assessment of changes in tissue architecture using a manual 4-point scale made at low magnification (10× objective), which considers the invasion of inflammatory cells such as neutrophils, macrophages and lympohocytes. Immunohistochemistry staining for cytokines and chemokines is performed to determine the underlying molecular mechanisms regulating these changes in tissue structure. Tumor specific markers and cell proliferation (ki67, cyclin D) and hypoxia biomarkers (GLUT1, CA9) is conducted and these data compared with tumor measurements from the SPECT/CT scanning. Blood serum samples are analyzed for treatment-induced changes in circulating cytokines using a Multiplex Bead Array Assay system for detection of soluble circulating cytokines (Luminex systems). This provides a comparison of response of tumor and normal tissues to the heat and radiation treatments.

EXAMPLE 3

Clinical Implementation

The system 10 described is employed on the investigations on small animals where the air volume circulated is relatively small and easy to control. For the clinical translation application, where human subject is involved, a heated breathing tube is employed to minimize air heat loss due the larger air volumes, and it is incorporated in the ventilator 14 and temperature control feedback loop 70.

Figure 3:
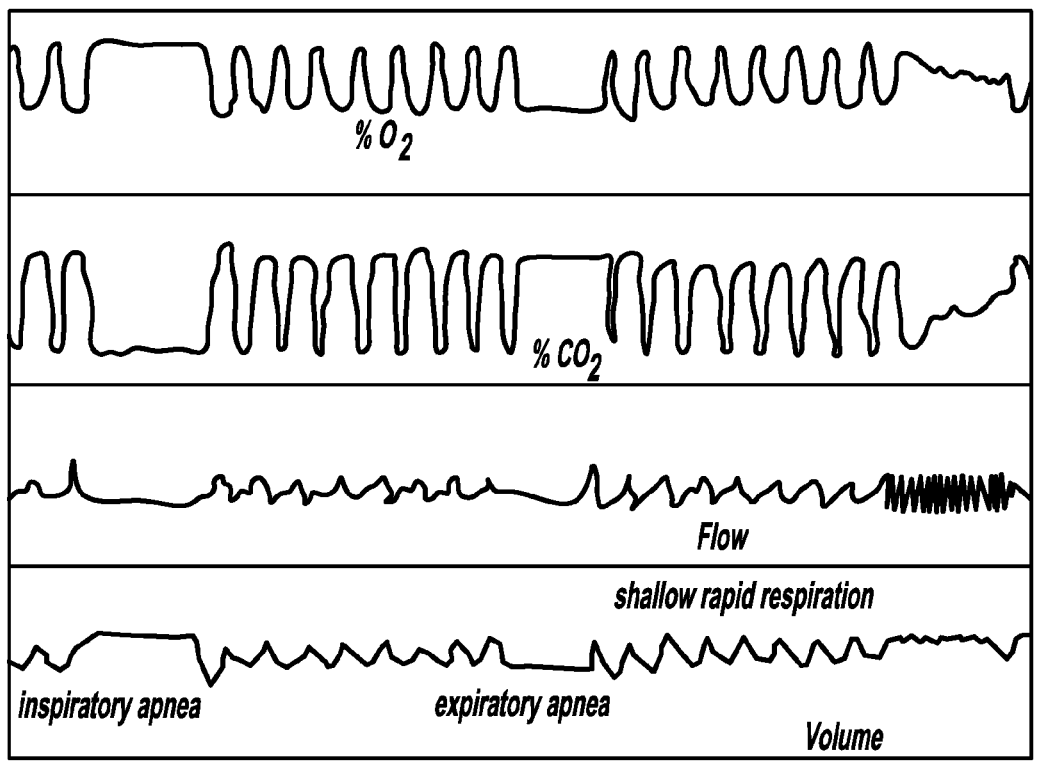
FIG. 3 shows a monitor screen for the system of FIG. 1 employed to monitor and record respiratory parameters.

Respiratory parameters (volume, flow, inhalation/exhalation pressure, $CO_2$, $O_2$ concentrations, temperature) are measured by the machine's mouthpiece 52 and results are displayed on the control room monitor, as displayed, for example, in FIG. 3. This provides a combination of parameters that can be used for gating a linear accelerator that provides a radiation source for radiotherapy.

If gating is employed (~5% of lung cancer cases) the clinician and the patient work together to establish the appropriate parameter to gate based on the patient's condition. This information is saved in a breathing coordinator system (such as the Active Breathing Coordinator™ system) as a patient-specific file. A comfortable patient is less likely to move during irradiation. Since the temperature controlled ventilator (TCV) 14 is designed to be fully portable, patients can practice with the device before treatment without tying up a treatment room unnecessarily. The patient can override the heating system using a thumb switch. The abort option gives the patient confidence and a sense of active participation in the treatment. Though the HART technique does not add significant additional time on to the treatment, routine clinical usage a user-friendly method in routine clinical usage is employed to quickly implement it.

The following references are incorporated herein by reference in their entirety:

1. Westermann A M, Jones E L, Schem B C, van der Steen-Banasik E, Koper P, Mella O et al. First results of triple-modality treatment combining radiotherapy, chemotherapy, and hyperthermia for the treatment of patients with stage IIB, III, and IVA cervical carcinoma. *Cancer* 2005; 104:763-70. PMID: 15968685
2. Hildebrandt B, Wust P. Interactions between hyperthermia and cytotoxic drugs. *Cancer Treat. Res.* 2007; 134:185-93. PMID: 17633054
3. Hehr T, Wust R, Bamberg M, Budach W. Current and potential role of thermoradiotherapy for solid tumours. *Onkologie* 2003; 26:295-302. PMID: 12845217
4. Dewhirst M W, Vujaskovic Z, Jones E, Thrall D. Re-setting the biologic rationale for thermal therapy. *International Journal of Hyperthermia* 2005; 21:779-90. PMID: 16338861
5. van der Zee J. Heating the patient: a promising approach? *Annals of Oncology* 2002; 13:1173-84. PMID: 12181239
6. Jones E L, Oleson J R, Prosnitz L R, Samulski T V, Vujaskovic Z, Yu D H et al. Randomized trial of hyperthermia and radiation for superficial tumors. *Journal of Clinical Oncology* 2005; 23:3079-85. PMID: 15860867
7. Wust P, Hildebrandt B, Sreenivasa G, Rau B, Gellermann J, Riess H et al. Hyperthermia in combined treatment of cancer. *Lancet Oncology* 2002; 3:487-97. PMID: 12147435 PMID: 12147435
8. Karino T, Koga S, Maeta M. Experimental studies of the effects of local hyperthermia on blood flow, oxygen pressure and pH in tumors. *Jpn. J. Surg.* 1988; 18:276-83. PMID: 3404776
9. Maeta M, Karino T, Inoue Y, Hamazoe R, Shimizu N, Koga S. The effect of angiotensin II on blood flow in tumours during localized hyperthermia. *Int. J. Hyperthermia* 1989; 5:191-7. PMID: 2926185
10. Horsman M R, Overgaard J. Can mild hyperthermia improve tumour oxygenation?*Int. J. Hyperthermia* 1997; 13:141-7. PMID: 9147141
11. Sorensen B S, Horsman M R, Vorum H, Honore B, Overgaard J, Alsner J. Proteins upregulated by mild and severe hypoxia in squamous cell carcinomas in vitro identified by proteomics. *Radiother. Oncol.* 2009; 92:443-9. PMID: 19541378
12. Menoret A, Chandawarkar R. Heat-shock protein-based anticancer immunotherapy: An idea whose time has come. *Seminars in Oncology* 1998; 25:654-60. PMID: 9865680
13. Tamura Y, Peng P, Liu K, Daou M, Srivastava P K. Immunotherapy of tumors with autologous tumor derived heat shock protein preparations. *Science* 1997; 278:117-20. PMID: 9311915
14. Suto R, Srivastava P K. A Mechanism for the Specific Immunogenicity of Heat-Shock Protein-Chaperoned Peptides. *Science* 1995; 269:1585-8. PMID: 7545313
15. DahmDaphi J, Brammer I, Dikomey E. Heat effects on the repair of DNA double-strand breaks in CHO cells. *International Journal of Radiation Biology* 1997; 72:171-9. PMID: 9269310
16. Dikomey E, Jung H. Correlation Between Thermal Radiosensitization and Slowly Rejoined Dna Strand Breaks in Cho Cells. *International Journal of Radiation Biology* 1995; 68:227-33. PMID: 7561382
17. Dikomey E, Franzke J. Effect of Heat on Induction and Repair of Dna Strand Breaks in X-Irradiated Cho Cells. *International Journal of Radiation Biology* 1992; 61:221-33. PMID: 1351910
18. Spiro I J, Denman D L, Dewey W C. Effect of Hyperthermia on Cho Dna-Polymerases Alpha and Beta. *Radiation Research* 1982; 89:134-49. PMID: 7063602

19. Hiraoka M, Masunaga S, Nishimura Y, Nagata Y, Jo S, Akuta K et al. Regional Hyperthermia Combined with Radiotherapy in the Treatment of Lung Cancers. *International Journal of Radiation Oncology Biology Physics* 1992; 22:1009-14. PMID: 1313403
20. Ohguri T, Imada H, Yahara K, Morioka T, Nakano K, Terashima H et al. Radiotherapy with 8-Mhz Radiofrequency-Capacitive Regional Hyperthermia for Stage Hi Non-Small-Cell Lung Cancer: the Radiofrequency-Output Power Correlates with the Intraesophageal Temperature and Clinical Outcomes. *International Journal of Radiation Oncology Biology Physics* 2009; 73:128-35. PMID: 18513887
21. Corry P M, Armour E P. The heat shock response: role in radiation biology and cancer therapy. *Int. J. Hyperthermia* 2005; 21:769-78. PMID: 16338860
22. Sekins K M, Leeper D B, Hoffman J K, Wolfson M R, Shaffer T H. Feasibility of lung cancer hyperthermia using breathable perfluorochemical (PFC) liquids. Part I: Convective hyperthermia. *Int. J. Hyperthermia* 2004; 20:252-77. PMID: 15204525
23. Sekins K M, Leeper D B, Hoffman J K, Keilman G W, Ziskin M C, Wolfson M R et al. Feasibility of lung cancer hyperthermia using breathable perfluorochemical (PFC) liquids. Part II: Ultrasound hyperthermia. *Int. J. Hyperthermia* 2004; 20:278-99. PMID: 15204526
24. Aoyagi Y, McLellan T M, Shephard R J. Interactions of physical training and heat acclimation—The thermophysiology of exercising in a hot climate. *Sports Medicine* 1997; 23:173-210. PMID: 9108637
25. Atkins K J, Thompson M W, Ward J J, Kelly P T. Expired air temperature during prolonged exercise in cool- and hot-humid environments. *European Journal of Applied Physiology and Occupational Physiology* 1997; 76:352-5. PMID: 9349651
26. Livingstone S D, Nolan R W, Cain J B, Keefe A A. Effect of Working in Hot Environments on Respiratory Air Temperatures. *European Journal of Applied Physiology and Occupational Physiology* 1994; 69:98-101. PMID: 7805678
27. Corry P M, Jabboury K, Kong J S, Armour E P, McCraw F J, Leduc T. Evaluation of equipment for hyperthermic treatment of cancer. *Int. J. Hyperthermia* 1988; 4:53-74. PMID: 3346584
28. Mclemore T L, Eggleston J C, Shoemaker R H, Abbott B J, Bohlman M E, Liu M C et al. Comparison of Intrapulmonary, Percutaneous Intrathoracic, and Subcutaneous Models for the Propagation of Human Pulmonary and Nonpulmonary Cancer Cell-Lines in Athymic Nude-Mice. *Cancer Research* 1988; 48:2880-6. PMID: 3359444
29. Mclemore T L, Liu M C, Blacker P C, Gregg M, Alley M C, Abbott B J et al. Novel Intrapulmonary Model for Orthotopic Propagation of Human-Lung Cancers in Athymic Nude-Mice. *Cancer Research* 1987; 47:5132-40. PMID: 3621199
30. Travis E L. The Sequence of Histological-Changes in Mouse Lungs After Single Doses of X-Rays. *International Journal of Radiation Oncology Biology Physics* 1980; 6:345-7. PMID: 7390907
31. Johnston C J, Williams J P, Elder A, Hernady E, Finkelstein J N. Inflammatory cell recruitment following thoracic irradiation. *Experimental Lung Research* 2004; 30:369-82. PMID: 15204829
32. Rubin P, Finkelstein J, Shapiro D. Molecular-Biology Mechanisms in the Radiation Induction of Pulmonary Injury Syndromes—Interrelationship Between the Alveolar Macrophage and the Septal Fibroblast. *International Journal of Radiation Oncology Biology Physics* 1992; 24:93-101. PMID:1512168
33. Hong J H, Chiang C S, Tsao C Y, Lin P Y, McBride W H, Wu C J. Rapid induction of cytokine gene expression in the lung after single and fractionated doses of radiation. *International Journal of Radiation Biology* 1999; 75:1421-7. PMID: 10597915
34. Rubin P, Johnston C J, Williams J P, Mcdonald S, Finkelstein J N. A Perpetual Cascade of Cytokines Postirradiation Leads to Pulmonary Fibrosis. *International Journal of Radiation Oncology Biology Physics* 1995; 33:99-109. PMID: 7642437
35. Mcdonald S, Rubin P, Phillips T L, Marks L B. Injury to the Lung from Cancer-Therapy—Clinical Syndromes, Measurable End-Points, and Potential Scoring Systems. *International Journal of Radiation Oncology Biology Physics* 1995; 31:1187-203. PMID: 7713782
36. Ashcroft T, Simpson J M, Timbrell V. Simple Method of Estimating Severity of Pulmonary Fibrosis on A Numerical Scale. *Journal of Clinical Pathology* 1988; 41:467-70. PMID: 3366935
37. Kasper M, Haroske G. Alterations in the alveolar epithelium after injury leading to pulmonary fibrosis. *Histology and Histopathology* 1996; 11:463-83. PMID: 8861769
38. Craciunescu O I, Stauffer P R, Soher B J, Wyatt C R, Arabe O, Maccarini P et al. Accuracy of real time noninvasive temperature measurements using magnetic resonance thermal imaging in patients treated for high grade extremity soft tissue sarcomas. *Med. Phys.* 2009; 36:4848-58. PMID: 19994492
39. Ishihara Y, Calderon A, Watanabe H, Okamoto K, Suzuki Y, Kuroda K et al. Precise and Fast Temperature Mapping Using Water Proton Chemical-Shift. *Magnetic Resonance in Medicine* 1995; 34:814-23. PMID: 8598808
40. de Senneville B D, Quesson B, Moonen C T W. Magnetic resonance temperature imaging. *International Journal of Hyperthermia* 2005; 21:515-31. PMID: 16147437
41. Gellermann J, Wlodarczyk W, Feussner A, Fahling H, Nadobny J, Hildebrandt B et al. Methods and potentials of magnetic resonance imaging for monitoring radiofrequency hyperthermia in a hybrid system. *International Journal of Hyperthermia* 2005; 21:497-513. PMID: 16147436
42. Galiana G, Branca R T, Jenista E R, Warren W S. Accurate temperature imaging based on intermolecular coherences in magnetic resonance. *Science* 2008; 322:421-4. PMID: 18927389

The foregoing as well as other embodiments are within the following claims:

The invention claimed is:

1. A method for locally inducing hyperthermia in lung tissue in a patient for radiation therapy comprising:
   modulating the temperature of air inhaled by the patient;
   modulating the humidity of the air inhaled by the patient;
   achieving hyperthermia in the lung tissue of the patient; and
   maintaining the humidity and temperature of the air inhaled by the patient.

2. The method of claim 1 wherein the modulated air temperature inhaled by the patient is between about 45° C. to 55° C.

3. The method of claim 1 wherein modulating the air temperature induces a thermal steady state in the patient's lung tissue with temperatures in the range of about 41° C. to 43° C.

4. The method of claim 1 wherein the modulated humidity of the air inhaled by the patient is less than about 65%.

5. The method of claim 4 wherein the modulated humidity of the air inhaled by the patient is less than about 60%.

6. The method of claim 1, wherein the temperature is modulated with at least one heating element.

7. The method of claim 1, wherein the humidity is modulated with at least one Peltier element.

8. The method of claim 1, wherein the humidity and temperature are maintained with at least one controller.

* * * * *